(12) United States Patent
Kim (10) Patent No.: US 12,122,475 B2
(45) Date of Patent: Oct. 22, 2024

(54) BICYCLE HANDLE GRIP FOR BODY COMPOSITION MEASUREMENT, SYSTEM, AND RECORDING MEDIUM USING THE BICYCLE HANDLE GRIP

(71) Applicant: Wrightbrothers Co., Ltd, Seoul (KR)

(72) Inventor: Hee Soo Kim, Seoul (KR)

(73) Assignee: Wrightbrothers Co., Ltd., Seoul (KR)

( * ) Notice: Subject to any disclaimer, the term of this patent is extended or adjusted under 35 U.S.C. 154(b) by 167 days.

(21) Appl. No.: 17/970,002

(22) Filed: Oct. 20, 2022

(65) Prior Publication Data

US 2023/0303200 A1     Sep. 28, 2023

(30) Foreign Application Priority Data

Mar. 24, 2022   (KR) .......................... 10-2022-0036518

(51) Int. Cl.
B62K 21/26         (2006.01)
(52) U.S. Cl.
CPC .................................. B62K 21/26 (2013.01)
(58) Field of Classification Search
CPC ..... B62K 21/26; A61B 5/0537; A61B 5/6895; A61B 5/4872; A61B 5/4875; A61B 5/4881; B62J 45/00
See application file for complete search history.

(56) References Cited

U.S. PATENT DOCUMENTS

| | | | |
|---|---|---|---|
| 4,319,581 A | 3/1982 | Cutter | |
| 5,337,753 A * | 8/1994 | Lekhtman | A61B 5/6887 600/519 |
| 6,450,922 B1 | 9/2002 | Henderson et al. | |
| 2008/0249421 A1* | 10/2008 | Twery | A63B 24/0062 600/481 |
| 2010/0210420 A1* | 8/2010 | Chang | A61B 5/6887 482/8 |
| 2011/0313310 A1* | 12/2011 | Tomita | A61B 5/389 600/546 |
| 2016/0150987 A1* | 6/2016 | Kwon | A61B 5/316 600/509 |

(Continued)

FOREIGN PATENT DOCUMENTS

| | | |
|---|---|---|
| CN | 206750041 U | 12/2017 |
| CN | 208625687 U | 3/2019 |

(Continued)

OTHER PUBLICATIONS

Translation of WO 2017003074 A1, Lee, May 1, 2017 (Year: 2017).*

(Continued)

*Primary Examiner* — Vinh Luong
(74) *Attorney, Agent, or Firm* — Bridgeway IP Law Group, PLLC; Jihun Kim (57) ABSTRACT

A handle grip for a bicycle, the handle grip including: a first grip portion coupled to a first side of a handlebar for the bicycle; a first electrode portion disposed to be exposed to the outside of the first grip portion so that the first electrode portion comes in contact with a first body surface of a user; a cable portion having one end connected to the first electrode portion and the other end extending outwardly from the first grip portion; and a module accommodating portion provided in a portion of the first grip portion and having a space for accommodating a predetermined electronic module.

16 Claims, 7 Drawing Sheets

(56) References Cited

U.S. PATENT DOCUMENTS

2019/0104955 A1* 4/2019 Kim .................... A61B 5/6895

FOREIGN PATENT DOCUMENTS

| EP | 3123932 A1 * | 2/2017 | ........... A61B 5/7221 |
|----|----|----|----|
| JP | 05337096 A | 12/1993 | |
| JP | 3180320 B2 | 6/2001 | |
| JP | 2001276025 A | 10/2001 | |
| JP | 3511587 B2 | 1/2004 | |
| KR | 20130059775 A | 6/2013 | |
| KR | 1020200038675 A | 4/2020 | |
| WO | WO-2004045723 A1 * | 6/2004 | ........... A61B 5/6887 |
| WO | 2017003074 A | 1/2017 | |

OTHER PUBLICATIONS

Translation of CN 208625687 U, Zhang, Mar. 22, 2019 (Year: 2019).*

Szekeres Gabor, "Extended European Search Report for European Application No. 22202076.0", Jul. 27, 2023, EPO, Munich, Germany.

"Office Action for Japanese patent application No. 2022-169668", Oct. 30, 2023, JPO, Japan.

Yoo Yeong Seok, "Office Actions for KR patent application No. 10-2022-0036518", Jun. 15, 2022, KIPO, Republic of Korea.

Yoo Yeong Seok, "Office Actions for KR patent application No. 10-2022-0036518", Sep. 19, 2022, KIPO, Republic of Korea.

Yoo Yeong Seok, "Notice of Allowance for KR patent application No. 10-2022-0036518", Oct. 31, 2022, KIPO, Republic of Korea.

* cited by examiner

BICYCLE HANDLE GRIP FOR BODY COMPOSITION MEASUREMENT, SYSTEM, AND RECORDING MEDIUM USING THE BICYCLE HANDLE GRIP

CROSS-REFERENCE TO RELATED APPLICATION

This application claims priority to Korean Patent Application No. 10-2022-036518, filed on Mar. 24, 2022. The entire contents of the application on which the priority is based are incorporated herein by reference.

TECHNICAL FIELD

An aspect of the present disclosure relates to a technology for checking body composition information of a user using a handle grip coupled to a handlebar for a bicycle and providing various linked services.

BACKGROUND

Recently, as the knowledge of medicine and health is widely distributed to the general public, interest in individual health care is increasing. In particular, in the past, individuals had to use medical devices that were mainly used in hospitals or examination institutions in order to check health of the individuals, but recently, as small medical devices and health care devices that can be possessed or carried by individuals have emerged, interest in medical devices that can be easily provided or used for measurement by the individuals has increased.

Among analysis schemes used to check an individual's health, body composition analysis is an analysis method for checking an individual's health status by analyzing water, fat, bone, muscle, or the like in a human body in a quantitative ratio.

Information on such a body composition has a variety of uses. For example, a person trying to do weight training can use body composition information to make an exercise plan, and the body composition information motivates the user by ascertaining or improving a problematic part of a body of an overweight or underweight person.

Thus, because the body composition information is widely utilized and is useful for self-healthcare, it is important to measure and monitor the body composition information periodically in real life.

SUMMARY

The present disclosure intends to periodically measure and monitor body composition information in real life through a bicycle, in consideration of the bicycle being positioned as a universal means of living for modern people.

In accordance with an aspect of the present disclosure, there is provided a handle grip for a bicycle. The handle grip comprises: a first grip portion coupled to a first side of a handlebar for the bicycle; a first electrode portion disposed to be exposed to the outside of the first grip portion so that the first electrode portion comes in contact with a first body surface of a user; a cable portion having one end connected to the first electrode portion and the other end extending outwardly from the first grip portion; and a module accommodating portion provided in a portion of the first grip portion and having a space for accommodating a predetermined electronic module.

The handle grip may comprises an electronic module operated to flow a current to the first electrode portion.

The electronic module may include a power supply unit configured to supply the current to the first electrode portion; a control unit configured to control the current supplied to the first electrode portion, and measure an electrical characteristic of the first electrode portion when a body of the user comes in contact with the first electrode portion; and a communications unit configured to transfer information on the electrical characteristic to an external device.

The control unit may perform control so that electricity is supplied to the first electrode portion, to measure an electrical characteristic flowing through the first electrode portion when a preset touch pattern is sensed in the first electrode portion.

The handle grip may include a second grip portion coupled to a second side of the handlebar for the bicycle; and a second electrode portion disposed outside the second grip portion so that the second electrode portion comes in contact with a palm of the user when the user grips the second grip portion.

The cable portion may connect the first electrode portion to the second electrode portion.

The first electrode portion may include a first input electrode and a first output electrode, and the second electrode portion may include a second input electrode and a second output electrode.

The cable portion may include a first wire configured to connect the first input electrode to the second input electrode; a second wire configured to connect the first output electrode to the second output electrode; and a outer insulation configured to electrically insulate the first wire and the second wire from each other.

The first grip portion may include a cutout portion formed by cutting out a portion of a material coupled to the handlebar in an axial direction of the handlebar so that the first grip portion is attachable to or detachable from the handlebar.

The module space is formed such that the first grip portion is located at a distal end portion of the handlebar in a state in which the first grip portion is coupled to the handlebar.

The first grip portion may include an inner grip portion and an outer grip portion configured to be opened and closed with reference to the module space.

The outer grip portion may be made to have a higher strength than that of the inner grip portion.

In accordance with another aspect of the present disclosure, there is provided a body composition measurement system. The system comprises: a handle grip including a first grip portion coupled to a first side of a handlebar for a bicycle, a first electrode portion disposed to be exposed to the outside of the first grip portion so that the first electrode portion comes in contact with a first body surface of a user, a cable portion having one end connected to the first electrode portion and the other end extending outwardly from the first grip portion, and an electronic module configured to perform control so that a current flows through the first electrode portion, measure an electrical characteristic of the first electrode portion, and transfer the electrical characteristic to a user terminal; and the user terminal including one or more memories configured to store instructions for performing a predetermined operation, and one or more processors operably connected to the one or more memories and operating to execute instructions for determining the body composition information of the user on the basis of the electrical characteristic.

The processor is configured to: receive a first electrical characteristic measured with the handle grip at a first point in time before the user rides the bicycle, and determine first body composition information, receive a second electrical characteristic measured with the handle grip at a second point in time after the user rides the bicycle, and determine second body composition information, and provide information derived newly by utilizing body composition change information generated by comparing the first body composition information with the second body composition information, and information on an event performed by the user between the first point in time and the second point in time.

The processor is configured to: store a course along which the user moves by a bicycle between the first point in time and the second point in time, derive a score by applying a predetermined algorithm to a degree of change in the first body composition information and the second body composition information, map the score to the course, and provide the score mapped for each course, in order to provide the newly derived information.

The processor is configured to: receive electrical characteristic measured with the handle grip for each date on which the user rides the bicycle to determine and store the body composition information for each date, store a bicycle use time, moving distance, and exercise course on the basis of real-time position information measured for each date on which the user uses the bicycle, and provide the bicycle use time, moving distance, exercise course, and body composition information for each date.

The processor is configured to: receive target body composition information and target date from the user, and compare the body composition information measured for each date with the target body composition information to recommend an amount of exercise, an exercise course, an exercise time, and an exercise distance to be performed to achieve the target body composition information by the target date.

The processor is configured to: receive the electrical characteristic measured with the handle grip by the user to determine the body composition information, analyze a muscle mass of a left arm, right arm, left leg, and right leg of the user on the basis of the determined body composition information, and recommend an exercise product for reinforcing a portion whose muscle mass is determined to be smaller than or equal to a preset value among the left arm, right arm, left leg, and right leg of the user.

The processor is configured to: receive target body composition information and target date from the user, and compare the body composition information measured for each date with the target body composition information to recommend an amount of exercise, an exercise course, an exercise time, and an exercise distance to be performed to achieve the target body composition information by the target date.

The processor is configured to: receive the electrical characteristic measured with the handle grip by the user to determine the body composition information, analyze a muscle mass of a left arm, right arm, left leg, and right leg of the user on the basis of the determined body composition information, and recommend an exercise product for reinforcing a portion whose muscle mass is determined to be smaller than or equal to a preset value among the left arm, right arm, left leg, and right leg of the user.

In accordance with another aspect of the present disclosure, there is provided a non-transitory computer-readable recording medium having a computer program stored therein, wherein the computer program comprising instructions for causing a processor to perform a method. The method comprises: receiving an electrical characteristic of a first electrode portion from a handle grip including a first grip portion coupled to a first side of a handlebar for a bicycle, the first electrode portion disposed to be exposed to the outside of the first grip portion so that the first electrode portion comes in contact with a first body surface of a user, a cable portion having one end connected to the first electrode portion and the other end extending outwardly from the first grip portion, and an electronic module configured to perform control so that a current flows through the first electrode portion, and measure the electrical characteristic of the first electrode portion; and determining body composition information of the user on the basis of the electrical characteristic, when the computer program is executed by the processor.

The determining of the body composition information of the user may include determining of the body composition information of the user includes: receiving a first electrical characteristic measured with the handle grip at a first point in time before the user rides the bicycle, and determining first body composition information; receiving a second electrical characteristic measured with the handle grip at a second point in time after the user rides the bicycle, and determining second body composition information; and providing information derived newly by utilizing body composition change information generated by comparing the first body composition information with the second body composition information, and information on an event performed by the user between the first point in time and the second point in time.

The providing of the newly derived information may include: storing a course along which the user moves by the bicycle between the first point in time and the second point in time; deriving a score by applying a predetermined algorithm to a degree of change in the first body composition information and the second body composition information; mapping the score to the course; and providing the score mapped for each course.

The determining of the body composition information of the user may include: receiving electrical characteristic measured with the handle grip for each date on which the user rides the bicycle to determine and store the body composition information for each date; receiving target body composition information and target date from the user; and comparing the body composition information measured for each date with the target body composition information to recommend an amount of exercise, an exercise course, an exercise time, and an exercise distance to be performed to achieve the target body composition information by the target date.

The determining of the body composition information of the user may include: receiving the electrical characteristic measured with the handle grip by the user to determine the body composition information, analyzing a muscle mass of a left arm, right arm, left leg, and right leg of the user on the basis of the determined body composition information, and recommending an exercise product for reinforcing a portion whose muscle mass is discriminated to be smaller than or equal to a preset value among the left arm, right arm, left leg, and right leg of the user.

In an aspect of the present disclosure, a structural feature of a bicycle itself that a handlebar of the bicycle comes in direct contact with a body surface of a user can be used in order to solve the above-described problem. According to the aspect of the present disclosure, a bicycle handle grip that enables measurement of body composition information of a user is coupled to a handlebar of a bicycle so that the body composition of the user using the bicycle can be easily measured, and a variety of linked services suitable for the user can be provided by using a result of the body composition measurement.

According to the aspect of the present disclosure, a user can easily perform body composition measurement on a bicycle of the user by simply replacing a handle grip of an existing bicycle.

In particular, when a bicycle has a handlebar that a user can grip with both hands irrespective of the type of bicycle, such as an outdoor bicycle that is used outdoors and a fitness bicycle that is used indoors for weight training, it is possible to easily perform body composition measurement by simply mounting the handle grip according to the aspect of the present disclosure on the handlebar and installing an application that works in conjunction with the handle grip in the user terminal.

Thus, according to the aspect of the present disclosure, it is possible to provide a variety of linked services, such as a service for recommending a course to users according to a big data result obtained by measuring body composition change information for each bicycle course, a service for scheduling daily exercise on the basis of body composition information of a user, and a service for recommending customized products depending on a body state of a user.

According to the aspect of the present disclosure, it is possible to suggest a new concept that a bicycle is used as a health care device capable of measuring body composition information anywhere through the bicycle, beyond use of a mobile device that can be encountered in real life to maintain health.

Effects that can be obtained in the present disclosure are not limited to the above-described effects, and other effects not described may be clearly understood by those skilled in the art to which the present disclosure belongs from description below.

DETAILED DESCRIPTION

The advantages and features of the embodiments and the methods of accomplishing the embodiments will be clearly understood from the following description taken in conjunction with the accompanying drawings. However, embodiments are not limited to those embodiments described, as embodiments may be implemented in various forms. It should be noted that the present embodiments are provided to make a full disclosure and also to allow those skilled in the art to know the full range of the embodiments. Therefore, the embodiments are to be defined only by the scope of the appended claims.

Terms used in the present specification will be briefly described, and the present disclosure will be described in detail.

In terms used in the present disclosure, general terms currently as widely used as possible while considering functions in the present disclosure are used. However, the terms may vary according to the intention or precedent of a technician working in the field, the emergence of new technologies, and the like. In addition, in certain cases, there are terms arbitrarily selected by the applicant, and in this case, the meaning of the terms will be described in detail in the description of the corresponding invention. Therefore, the terms used in the present disclosure should be defined based on the meaning of the terms and the overall contents of the present disclosure, not just the name of the terms.

When it is described that a part in the overall specification "includes" a certain component, this means that other components may be further included instead of excluding other components unless specifically stated to the contrary.

In addition, a term such as a "unit" or a "portion" used in the specification means a software component or a hardware component such as FPGA or ASIC, and the "unit" or the "portion" performs a certain role. However, the "unit" or the "portion" is not limited to software or hardware. The "portion" or the "unit" may be configured to be in an addressable storage medium, or may be configured to reproduce one or more processors. Thus, as an example, the "unit" or the "portion" includes components (such as software components, object-oriented software components, class components, and task components), processes, functions, properties, procedures, subroutines, segments of program code, drivers, firmware, microcode, circuits, data, database, data structures, tables, arrays, and variables. The functions provided in the components and "unit" may be combined into a smaller number of components and "units" or may be further divided into additional components and "units".

Hereinafter, the embodiment of the present disclosure will be described in detail with reference to the accompanying drawings so that those of ordinary skill in the art may easily implement the present disclosure. In the drawings, portions not related to the description are omitted in order to clearly describe the present disclosure.

Figure 1:
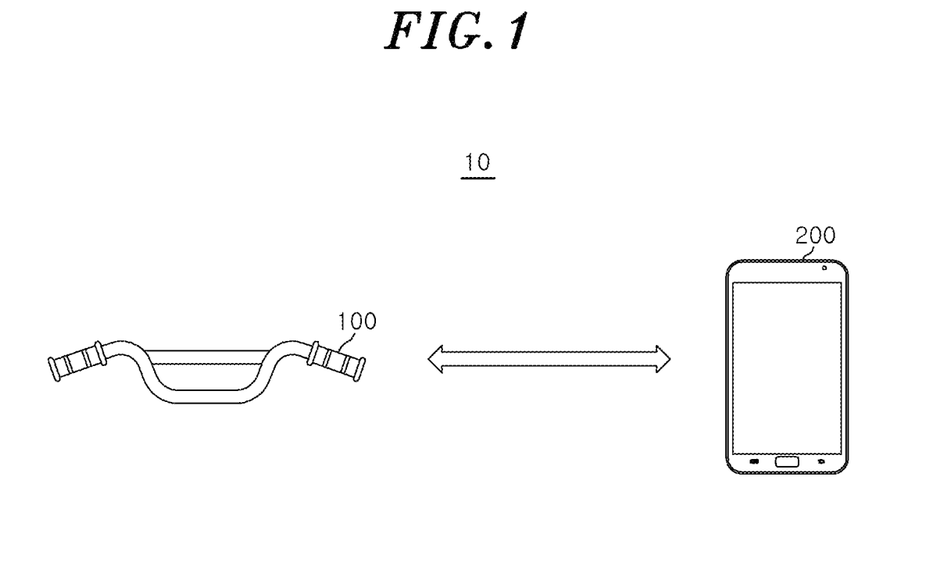
FIG. 1 is a configuration diagram of a body composition measurement system according to an embodiment.

FIG. 1 is a configuration diagram of a body composition measurement system 10 according to an embodiment.

Referring to FIG. 1, the body composition measurement system 10 according to the embodiment may include a bicycle handle grip for body composition measurement 100 (hereinafter referred to as a 'handle grip 100'), and a user terminal 200.

The handle grip 100 may be coupled to a first side (for example, a handlebar side gripped by a left hand) and a second side (for example, a handlebar side gripped by a right hand) of a bicycle handlebar. When a user grips the handle grip 100 and a body surface of the user comes in contact with the handle grip 100, the handle grip 100 can allow a predetermined amount of current (for example, low-energy alternating current waves) to flow to a body of the user and measure a current flowing in a circuit or a corresponding voltage to measure various electrical characteristics (for example, bioelectrical impedance) of the body of the user. For example, in a state in which an electrode included in the handle grip 100 is in contact with the body of the user, the handle grip 100 may allow a current to flow through the electrode to measure the electrical characteristic of the user. The handle grip 100 may transmit information on the electrical characteristic of the user to the user terminal 200.

The user terminal 200 may receive the information on the electrical characteristic of the user from the handle grip 100, and analyze the body composition information (for example, a body fat mass, body fat percentage, protein mass, body water mass, muscle mass, BMI value, and the like) of the user. The user terminal 200 may provide various linked services suitable for the user on the basis of the analyzed body composition information.

The user terminal 200 may be implemented as any type of device capable of performing an operation through a processor and transmitting or receiving information over a network. For example, the user terminal 200 may include a portable communications device, a smart phone, a computer device, a portable multimedia device, a notebook computer, a tablet PC, or the like.

The handle grip 100 and the user terminal 200 may communicate with each other through various communications schemes to transmit or receive data. For example, a communications scheme such as Bluetooth, NB-IoT, WiFi, 3G, LTE, or 5G may be used, but the present disclosure is not limited thereto and any present or future communications scheme may be applied.

Hereinafter, sides to which the handle grip 100 is coupled between left and right sides of a bicycle handlebar will be divided and shown as the terms 'first side' and 'second side'. In the embodiment of the present disclosure, the first side is a left handlebar side, and the second side is a right handlebar side. Alternatively, the embodiment of the present disclosure may also be applied to a case in which the first side is the right handlebar side and the second side is the left handlebar side.

Figure 2:
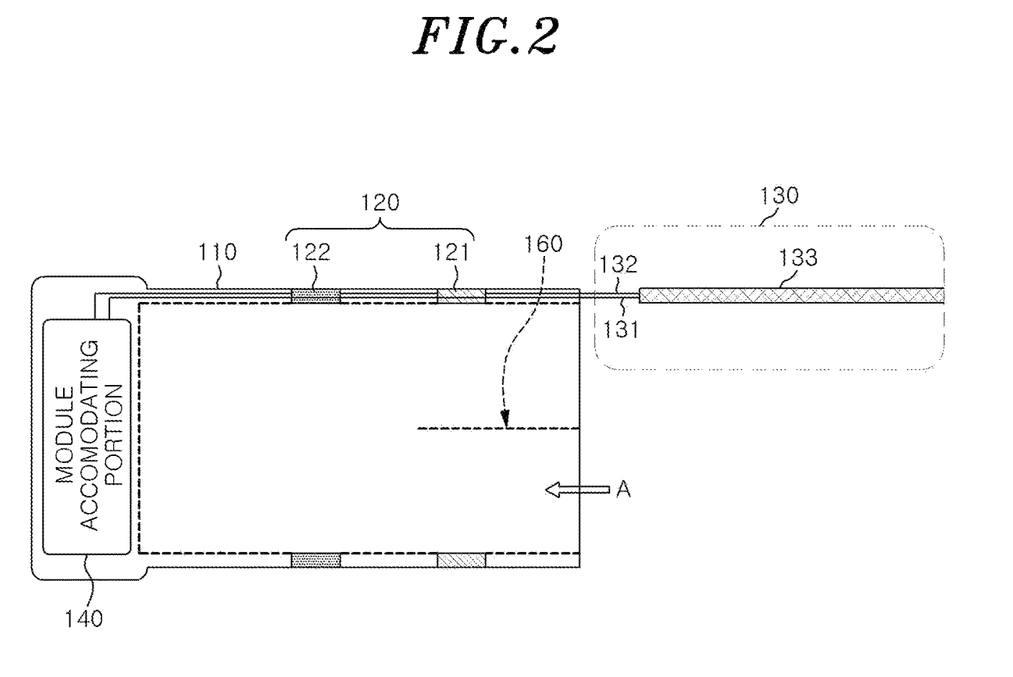
FIG. 2 is a first side cross-sectional view of a bicycle handle grip for body composition measurement according to an embodiment.

FIG. 2 is a first side cross-sectional view of a bicycle handle grip 100 for body composition measurement according to the embodiment.

Referring to FIG. 2, the handle grip 100 according to the embodiment may include a first grip portion 110, a first electrode portion 120, a cable portion 130, and a module accommodating portion 140.

The first grip portion 110 is a frame of the handle grip 100 coupled to the first side of the bicycle handlebar. The first grip portion 110 may be coupled to the first side of the bicycle handlebar in a direction A. The first grip portion 110 may be provided in a hollow form so that the first grip portion 110 can be coupled to fit a form of a left (or right) distal end frame of the bicycle handlebar, that is, to surround the frame of the handlebar. For example, when the bicycle handlebar is configured in a cylindrical frame and the distal end frame of the bicycle handlebar is configured in a straight form, the first grip portion 110 may be configured to form a reception space in which the cylindrical frame configured in a straight form can be received therein. As another example, when the distal end frame of the bicycle handlebar is configured to be bent in an arch form, the first grip portion 110 may be configured in a form of the distal end frame, that is, an arch form, and may be configured to form a reception space in which the frame in the arch form can be received therein.

The first grip portion 110 may be made of an elastic rubber or sponge material. The first grip portion 110 includes a cutout portion 160 (for example, refer to 111 in FIG. 6) that is formed by cutting out a portion of the material coupled to the bicycle handlebar in an axial direction of the bicycle handlebar so that the first grip portion 110 is attachable to or detachable from the bicycle handlebar. The first grip portion 110 may cover the frame of the handlebar when the cutout portion 160 is opened, and the first grip portion 110 may be fixed in a state in which the first grip portion 110 covers the handlebar frame due to the property of the elastic rubber material. The first grip portion 110 may further include a screw coupling configuration for preventing the cutout portion 160 from being opened with reference to the cutout portion 160 so that the first grip portion 110 can be fixed in a state in which the first grip portion 110 covers the handlebar frame.

The first electrode portion 120 may be configured to be exposed to the outside of the first grip portion 110 so that the first electrode portion 120 can come in contact with a first body surface (for example, a left hand) of the user when the user grips the first grip portion 110. For example, the first electrode portion 120 may be made in a ring form to surround the outside of the first grip portion 110. For example, when the first grip portion 110 includes the cutout portion 160, the first electrode portion 120 may be made in the form of a ring that is broken by a spacing of the cutout portion 160.

For example, the first electrode portion 120 may include a first input electrode 121 and a first output electrode 122. For example, the first input electrode 121 is disposed to come in contact with a thumb of the left hand of the user, and the first output electrode 122 is disposed to come in contact with a palm of the left hand of the user, when the user grips the first grip portion 110 with the left hand. Alternatively, the first input electrode 121 may be disposed to come in contact with the palm of the left hand of the user, and the first output electrode 122 may be disposed to come in contact with the thumb of the left hand of the user, when the user grips the first grip portion 110 with the left hand. That is, a disposition order of the first input electrode 121 and the first output electrode 122 disposed in the first grip portion 110 may be changed according to a design. A type and configuration of the electrodes included in the first electrode portion 120 are not limited to the above-described example, and may be modified into various embodiments according to an applied body composition measurement scheme.

The cable portion 130 includes one end connected to the first electrode portion 120, and the other end extending outwardly from the first grip portion 110 to be connected to an electrode that comes in contact with a second body surface (for example, a right hand) different from the first body surface of the user.

The module accommodating portion 140 may include a space formed in a portion of the first grip portion 110 so that a predetermined electronic module 150 can be mounted therein. For example, the module accommodating portion 140 may be formed to be located at a distal end portion of the bicycle handlebar (for example, at a position of the module accommodating portion 140 illustrated in FIG. 2) in a state in which the first grip portion 110 is coupled to the bicycle handlebar.

Figure 3:
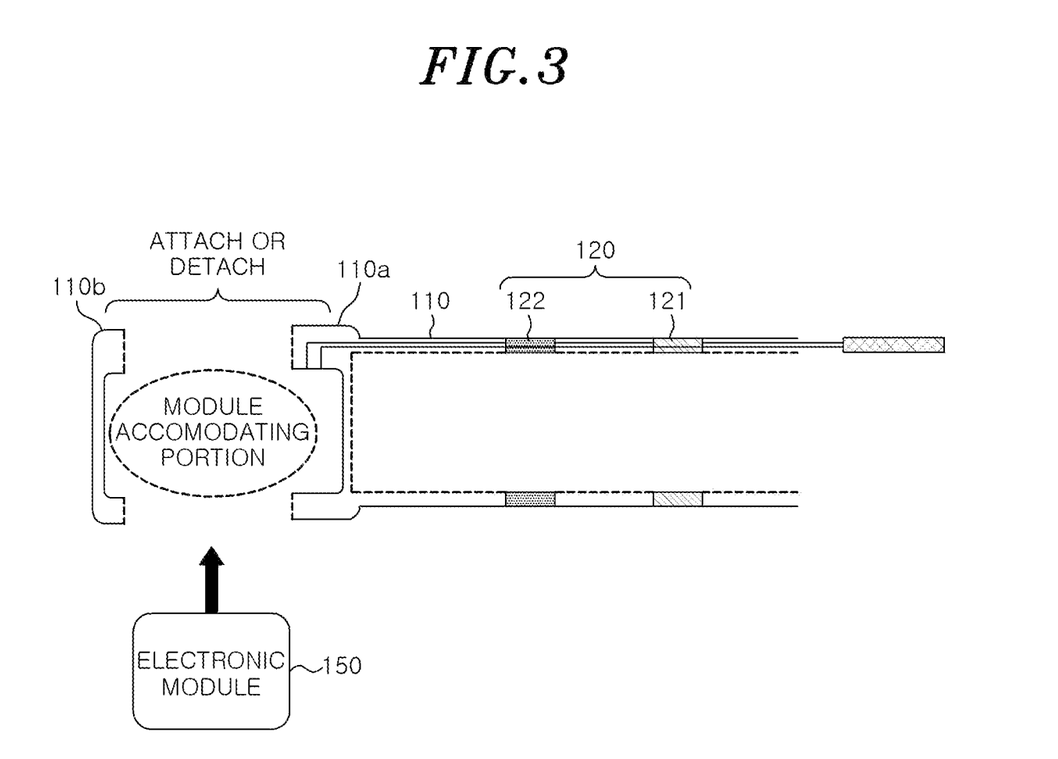
FIG. 3 is an illustrative diagram illustrating a structure in which a first grip portion of the bicycle handle grip for body composition measurement according to the embodiment of the present disclosure is configured of an inner grip portion and an outer grip portion so that a module space is opened and closed.

FIG. 3 is an illustrative diagram illustrating a structure in which the first grip portion 110 of the bicycle handle grip 100 for body composition measurement according to the embodiment is configured to an inner grip portion 110a and an outer grip portion 110b so that the module accommodating portion 140 is opened and closed.

Referring to FIG. 3, the first grip portion 110 may be made in a structure in which the module accommodating portion 140 is opened and closed so that the predetermined electronic module 150 can be mounted in or separated from the module accommodating portion 140. For example, the first grip portion 110 may include the inner grip portion 110a and the outer grip portion 110b that are opened and closed with reference to the position of the module accommodating portion 140.

The inner grip portion 110a and the outer grip portion 110b may have a structure in which the inner grip portion 110a and the outer grip portion 110b are coupled to or separated from each other through various schemes. For example, coupling surfaces of the inner grip portion 110a and the outer grip portion 110b may have a structure in which the coupling surfaces have a screw thread form and are coupled when turned in a clockwise direction and separated when turned in a counterclockwise direction. Alternatively, the contact surfaces of the inner grip portion 110a and the outer grip portion 110b may include N and S pole magnetic materials so that the contact surfaces are magnetically coupled, and the magnetic coupling may be released by applying an external force. Alternatively, a screw coupling configuration for the inner grip portion 110a and the outer grip portion 110b may be further included so that the contact surfaces can be coupled to and separated from each other. Through a structure of the first grip portion 110 including the inner grip portion 110a and the outer grip portion 110b, when a problem occurs in the electronic module 150 or a battery needs to be replaced, the user can easily repair or replace the electronic module 150 by releasing the coupling between the inner grip portion 110a and the outer grip portion 110b. On the other hand, when a problem occurs in the first grip portion 110, the user may reuse the existing electronic module 150 in a new first grip portion 110.

Further, a material of the outer grip portion 110b may be made with a strength (for example, at least one of tensile strength, compressive strength, bending strength, shear strength, and torsional strength) higher than that of the inner grip portion 110a. Accordingly, even when the bicycle falls and an impact is applied to the outer grip portion 110b, the outer grip portion 110b absorbs the impact that may be applied to the module space 140, thereby protecting the electronic module 150 from external impact.

Further, a material of the inner grip portion 110a surrounding the module space 140 in the inner grip portion 110a may be made with a strength (for example, at least one of tensile strength, compressive strength, bending strength, shear strength, and torsional strength) higher than that at a position at which the user grips the first grip portion with the hand among positions on the first grip portion. Accordingly, even when an impact is applied to the handle grip 100, a portion surrounding the module space 140 absorbs the impact, thereby protecting the electronic module 150.

Figure 4:
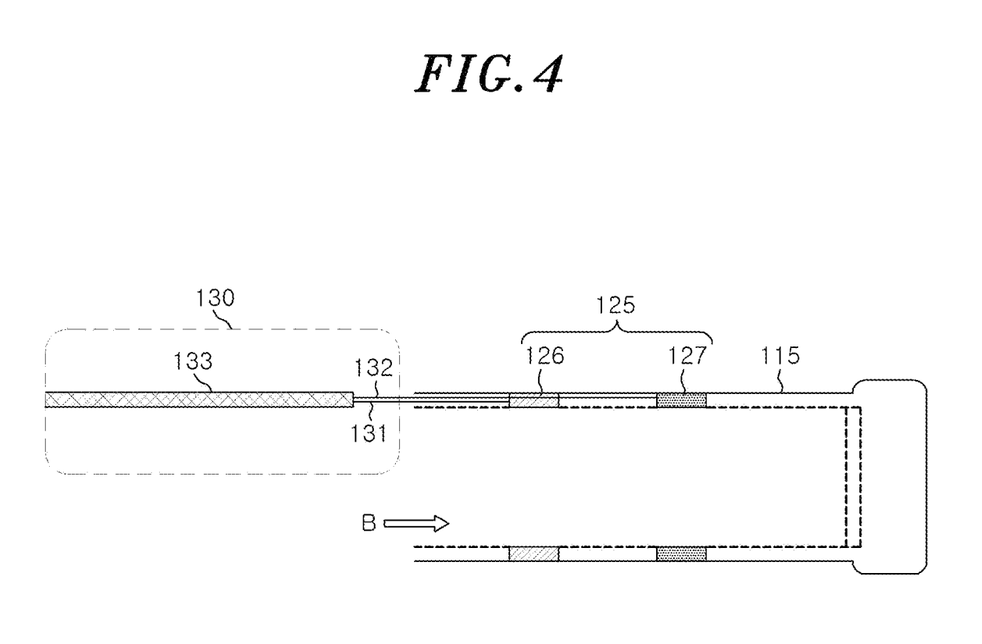
FIG. 4 is a second side cross-sectional view of the bicycle handle grip for body composition measurement according to the embodiment.

FIG. 4 is a second side cross-sectional view of the bicycle handle grip for body composition measurement 100 according to the embodiment. The handle grip 100 according to the embodiment may further include a second grip portion 115 and a second electrode portion 125 in FIG. 4, in addition to the configuration illustrated in FIG. 2.

Referring to FIG. 4, the second grip portion 115 is a frame of the handle grip 100 coupled to the second side of the bicycle handlebar. The second grip portion 115 may be coupled to the second side of the bicycle handlebar in a direction B. The second grip portion 115 may be made in a hollow form so that the second grip portion 115 can be coupled to fit a form of the right (or left) distal end frame of the bicycle handlebar, that is, so that the second grip portion 115 surrounds the frame of the handlebar. For example, when the handle grip 100 is used in a case in which the distal end frame of the bicycle handlebar has a straight form, the second grip portion 115 may be made to have a hollow form in a long cylindrical form. For example, when the handle grip 100 is used in a case in which the distal end frame of the bicycle handlebar is bent in an arch form, the second grip portion 115 may be made to have a hollow form in an arch form.

The second grip portion 115 may be made of an elastic rubber or sponge material. The second grip portion 115 includes a cutout portion 160 that is formed by cutting out a portion of the material coupled to the bicycle handlebar in the axial direction of the bicycle handlebar so that the second grip portion 115 is attachable to or detachable from the bicycle handlebar. The second grip portion 115 may cover the frame of the handlebar when the cutout portion 160 is opened, and the second grip portion 115 may be fixed in a state in which the second grip portion 115 covers the handlebar frame due to the property of the elastic rubber material. The second grip portion 115 may further include a screw coupling configuration for preventing the cutout portion 160 from being opened with reference to the cutout portion 160 so that the second grip portion 115 can be fixed in a state in which the second grip portion 115 covers the handlebar frame.

The second electrode portion 125 is configured to be exposed to the outside of the second grip portion 115 so that the second electrode portion 125 can come in contact with the second body surface (for example, the right hand) of the user when the user grips the second grip portion 115. For example, the second electrode portion 125 may be made in a ring form surrounding the outside of the second grip portion 115. For example, when the second grip portion 115 includes the cutout portion 160, the second electrode portion 125 may be made in the form of a ring that is broken by a spacing of the cutout portion 160.

For example, the second electrode portion 125 may include a second input electrode 126 and a second output electrode. For example, the second input electrode 126 may be disposed to come in contact with a thumb of the right hand of the user, and the second output electrode may be disposed to come in contact with a palm of the right hand of the user. Alternatively, the second input electrode 126 may be disposed to come in contact with the palm of the right hand of the user, and the second output electrode may be disposed to come in contact with the thumb of the right hand of the user, when the user grips the second grip portion 115 with the right hand. That is, a disposition order of the second input electrode 126 and the second output electrode disposed in the second grip portion 115 may be changed according to a design. A type and configuration of the electrodes included in the second electrode portion 125 are not limited to the above-described example, and may be modified into various embodiments according to an applied body composition measurement scheme.

The cable portion 130 illustrated in FIG. 4 may be configured to extend from the cable portion 130 illustrated in FIG. 2. Referring to FIGS. 2 and 4, the cable portion 130 includes a first wire 131 that connects the first input electrode 121 to the second input electrode 126; a second wire 132 that connects the first output electrode 122 to the second output electrode; and a outer insulation 133 configured to electrically insulate the first wire 131 and the second wire 132 from each other and to protect (for example, waterproof)

the first wire 131 and the second wire 132 from external impact or inflow of foreign substances.

A case in which the first electrode portion 120 and the second electrode portion 125 described in the embodiment of the present disclosure have two electrodes is illustrated, but the number and configuration of the illustrated electrodes are only examples for understanding, and various types of configurations such as the use of four electrodes may also be included as embodiments of the present disclosure according to a body composition measurement scheme.

Figure 5:
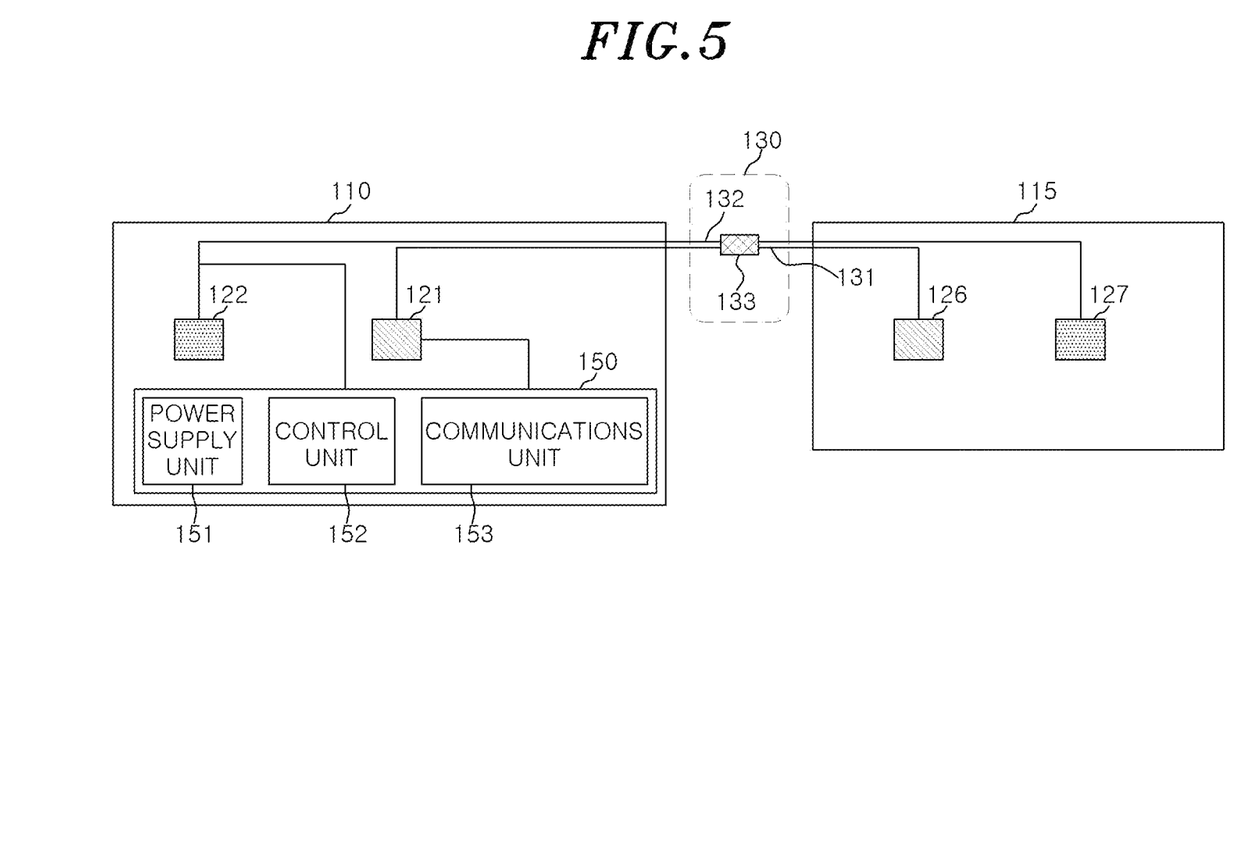
FIG. 5 is a circuit diagram of the bicycle handle grip for body composition measurement according to the embodiment.

FIG. 5 is a circuit diagram of the bicycle handle grip for body composition measurement 100 according to the embodiment.

Referring to FIG. 5, the handle grip 100 includes the first grip portion 110 coupled to the first side of the bicycle handlebar, the second grip portion 115 coupled to the second side of the bicycle handlebar, and the cable portion 130 that electrically connects the first grip portion 110 to the second grip portion 115.

The first grip portion 110 may include the first input electrode 121, the first output electrode 122, and the electronic module 150 disposed in the module space 140. The second grip portion 115 may include the second input electrode 126 and the second output electrode. The cable portion 130 may include the first wire 131 that connects the first input electrode 121 to the second input electrode 126; the second wire 132 that connects the first output electrode 122 to the second output electrode; and the outer insulation 133 configured to electrically insulate the first wire 131 and the second wire 132 from each other.

The electronic module 150 may be operated so that current flows from the first electrode portion 120 to the second electrode portion 125 when the user grips the first grip portion 110 and the second grip portion 115.

The electronic module 150 according to the embodiment may include a power supply unit 151, a control unit 152, and a communications unit 153.

The power supply unit 151 may include a battery that supplies power in order to supply a current to the first electrode portion 120. The power supply unit 151 may be connected to an external charging device that converts physical energy of a bicycle pedal into electrical energy and be charged in a self-charging manner. The control unit 152 may control a characteristic of the current supplied to the first electrode portion 120 and may measure an electrical characteristic of the first electrode portion 120 when electricity flows through the first input electrode 121, the second input electrode 126, the second output electrode, and the first output electrode 122 in a state in which the body of the user is in contact with the first electrode portion 120. The communications unit 153 may transfer information on the electrical characteristic to an external device. The electronic module 150 may further include a memory that stores instructions for operations of the power supply unit 151, the control unit 152, and the communications unit 153.

According to an embodiment, when the user grips the first grip portion 110 and the second grip portion 115 and the electronic module 150 allows a current to flow to the first input electrode 121, the current circulates through the first input electrode 121, the second input electrode 126, the second output electrode, and the first output electrode 122 because the first input electrode 121 and the first output electrode 122 are electrically connected by the left hand of the user and the second input electrode 126 and the second output electrode are electrically connected by the right hand of the user. In this case, the electronic module 150 can measure an electrical characteristic (for example, bio-impedance of the user) flowing through the first input electrode 121, the second input electrode 126, the second output electrode, and the first output electrode 122.

When a preset touch pattern of the user is sensed in the first electrode portion 120, the control unit 152 may perform control so that electricity is supplied to the first electrode portion 120, and measure an electrical characteristic flowing through the first electrode portion 120. For example, the preset touch pattern of the user may include a combination according to an input of at least one of a short touch and a long touch. For example, the preset touch pattern of the user may include an input of a predetermined number of short touches, an input of a predetermined number of long touches, a cross input of short touches and long touches, and the like. As another example, the preset touch pattern of the user may be a combination of the short touch or the long touch, and may be configured on the basis of Morse code. For example, in an embodiment of the present disclosure, the short touch may be a touch input generated for less than a predetermined first time (for example, 100 ms), and the long touch may be a touch input generated for the predetermined first time (for example, 100 ms) or more.

In the circuit of FIG. 5, information on a characteristic of a current applied to the handle grip 100 in order to analyze body composition information of a human and an electrical characteristic measured by the circuit is not limited to the illustrated embodiment, and various embodiments of an existing body composition measurement scheme or a future body composition measurement scheme can be applied for implementation.

Figure 6:
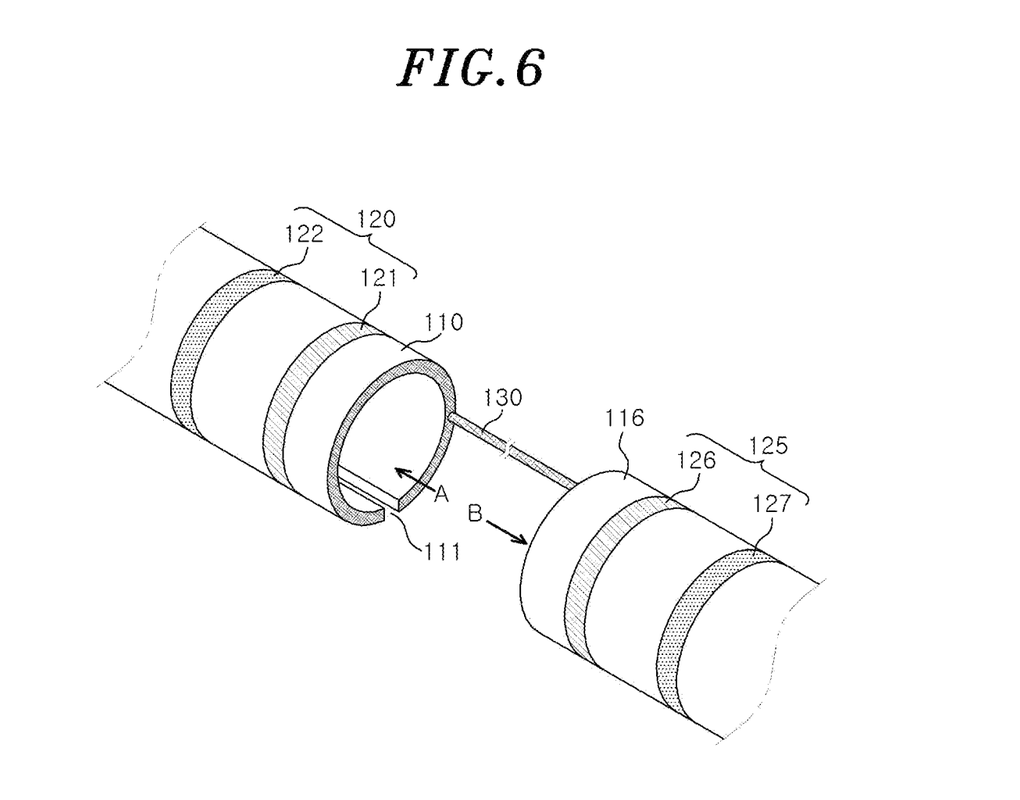
FIG. 6 is a perspective view of the bicycle handle grip for body composition measurement according to the embodiment.

FIG. 6 is a perspective view of the bicycle handle grip for body composition measurement 100 according to the embodiment.

Referring to FIG. 6, the first grip portion 110 or the second grip portion 115 may include a cutout portion 111 formed by cutting out a part of the material coupled to the bicycle handlebar in the axial direction of the bicycle handlebar so that the first grip portion 110 or the second grip portion 115 is attached to or detachable from the bicycle handlebar. The first grip portion 110 may be coupled to the first side of the bicycle handlebar in the direction A. The second grip portion 115 may be coupled to the second side of the bicycle handlebar in the direction B.

Figure 7:
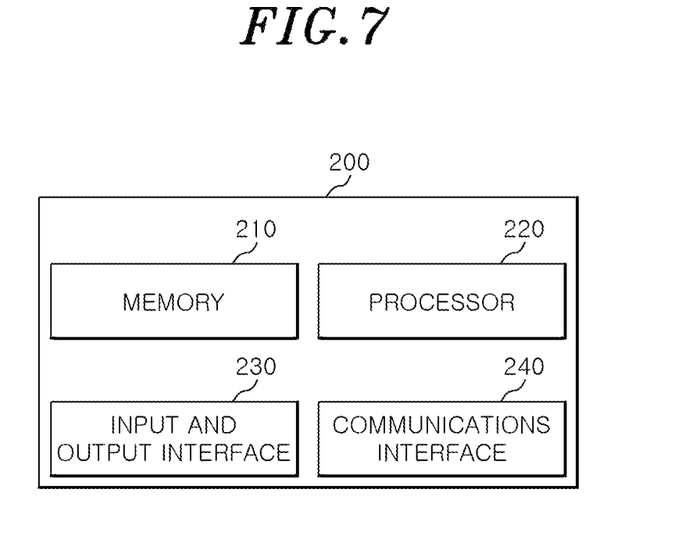
FIG. 7 is a functional block diagram of a user terminal according to an embodiment.

FIG. 7 is a functional block diagram of the user terminal 200 according to the embodiment.

Referring to FIG. 7, the user terminal 200 may include a memory 210, a processor 220, an input and output interface 230, and a communications interface 240.

The memory 210 may store instructions capable of causing an operation of the processor 220 to be performed. For example, the memory 210 may store computer code for performing an operation corresponding to the operation of the processor 220 described below.

The processor 220 may control an overall operation of the user terminal 200. The operation of the user terminal 200 illustrated in an embodiment described below may be understood as the operation of the processor 220.

The input and output interface 230 may include a hardware interface or a software interface that allows a user who controls the user terminal 200 to input specific information, or outputs specific information to the user.

The communications interface 240 enables the user terminal 200 to transmit and receive information to and from the handle grip 100 through a communications network. To this end, the communications interface 240 may include a wireless communications module or a wired communications module.

The user terminal 200 may store user information including information on age, sex, height, and weight of the user. The user terminal 200 can discriminate the body composition information (for example, the body fat mass, the body fat percentage, the protein mass, the body water mass, the muscle mass, the BMI value, and the like) of the user from the information on the electrical characteristic received from the handle grip 100 and the user information. As a scheme in which the user terminal 200 analyzes the body composition information of the user from the information on the electrical characteristic and the user information, various existing body composition analysis schemes may be applied.

The user terminal 200 may provide various linked services suitable for the user by using the body composition measurement result.

According to an embodiment, the user terminal 200 can receive a first electrical characteristic measured with the handle grip 100 at a first point in time before the user rides the bicycle, discriminate first body composition information, receive a second electrical characteristic measured with the handle grip 100 at a second point in time after the user rides the bicycle, and discriminate second body composition information. The user terminal 200 can provide information derived newly by utilizing 'body composition change information' generated by comparing the first body composition information with the second body composition information, and 'information on an event' performed while using a bicycle during a period in which the user measures the first body composition information and the second body composition information.

For example, the event information may include information on a course along which the user moves by bicycle between the first point in time and the second point in time. The course information may be generated on map information on the basis of real-time position information tracked by the user terminal 200 while the user rides the bicycle. The user terminal 200 may derive a score by applying a predetermined algorithm to a degree of change in the first body composition information and the second body composition information. For example, the user terminal 200 may use an algorithm for calculating a higher score when a degree of change in any one of the body fat mass, the body fat percentage, the protein mass, the body water mass, the muscle mass, and the BMI value increases during the period in which the first body composition information and the second body composition information are measured. The user terminal 200 may map the calculated score to a course along which the user moves, and store the score. The user terminal 200 may share the score mapped to the course with other users. The users can be assisted in objectively determining which course is good for body composition change on the basis of the score mapped to the course.

According to an embodiment, the user terminal 200 may receive electrical characteristic measured with the handle grip 100 for each date on which the user rides the bicycle, and discriminate and store the body composition information for each date. The user terminal 200 may provide an exercise scheduling service based on the body composition information for each date.

For example, the user terminal 200 may store a bicycle use time, moving distance, exercise course, and body composition information on the basis of real-time position information for each date on which the user uses the bicycle, and provides the user with information on a change transition of the body composition information. The user may input target body composition information and target date of the user to the user terminal 200. For example, the target body composition information may include any one of the body fat mass, the body fat percentage, the protein mass, the body water mass, the muscle mass, and the BMI value targeted by the user. The target date may include time information consisting of year, month, and day. The user terminal 200 may compare the target body composition information with the body composition information measured for each date, and recommend an amount of exercise, an exercise course, an exercise time, and an exercise distance to be performed to achieve the target body composition information by the target date.

According to an embodiment, the user terminal 200 may perform an operation for receiving the electrical characteristic measured with the handle grip 100 by the user, discriminating body composition information, and providing product information necessary for the user on the basis of the discriminated body composition information.

For example, the user terminal 200 may analyze a muscle mass of a left arm, right arm, left leg, and right leg of the user on the basis of the discriminated body composition information. The user terminal 200 may recommend an exercise product for reinforcing a portion whose muscle mass is discriminated to be smaller than or equal to a preset value among the left arm, the right arm, the left leg, and the right leg of the user. The user terminal 200 may recommend an exercise product for reinforcing a portion whose fat mass is discriminated to be equal to or larger than a preset value among the left arm, the right arm, the left leg, and the right leg of the user. The user terminal 200 may provide product information to the user in conjunction with an external DB server that stores product information used to increase the muscle mass of each of the left arm, the right arm, the left leg, and the right leg or to decrease the fat mass thereof.

According to an embodiment, the user terminal 200 may perform a setting so that the handle grip 100 operates when the input pattern is sensed in the handle grip 100, according to an input pattern set by the user. For example, the user terminal 200 may receive a predetermined touch pattern from the user and transmit information on the touch pattern to the handle grip 100. The handle grip 100 may store the received information on the touch pattern. Thereafter, when the input pattern of the user is sensed in the handle grip 100, the handle grip 100 may perform control so that electricity is supplied to the first electrode portion 120 and measure the electrical characteristic flowing through the first electrode portion 120.

According to the above-described embodiment, the user can easily perform the body composition measurement on the bicycle of the user by simply replacing a handle grip 100 of an existing bicycle. In particular, when a bicycle has a handlebar that a user can grip with both hands irrespective of the type of bicycle, such as an outdoor bicycle that is used outdoors and a fitness bicycle that is used indoors for weight training, it is possible to easily perform the body composition measurement by simply mounting the handle grip 100 according to the embodiment of the present disclosure on the handlebar and installing an application that works in conjunction with the handle grip 100 in the user terminal 200.

Thus, according to the embodiment of the present disclosure, it is possible to provide a variety of linked services, such as a service for recommending a course to users according to a big data result obtained by measuring body composition change information for each bicycle course, a service for scheduling daily exercise on the basis of body composition information of a user, and a service for recommending customized products depending on a body state of a user. According to the embodiment of the present disclosure, it is possible to suggest a new concept that a bicycle is used as a health care device capable of measuring body composition information anywhere through the bicycle, beyond use of a mobile device that can be encountered in real life to maintain health.

Combinations of steps in each flowchart attached to the present disclosure may be executed by computer program instructions. Since the computer program instructions can be mounted on a processor of a general-purpose computer, a special purpose computer, or other programmable data processing equipment, the instructions executed by the processor of the computer or other programmable data processing equipment create a means for performing the functions described in each step of the flowchart. The computer program instructions can also be stored on a computer-usable or computer-readable storage medium which can be directed to a computer or other programmable data processing equipment to implement a function in a specific manner. Accordingly, the instructions stored on the computer-usable or computer-readable recording medium can also produce an article of manufacture containing an instruction means which performs the functions described in each step of the flowchart. The computer program instructions can also be mounted on a computer or other programmable data processing equipment. Accordingly, a series of operational steps are performed on a computer or other programmable data processing equipment to create a computer-executable process, and it is also possible for instructions to perform a computer or other programmable data processing equipment to provide steps for performing the functions described in each step of the flowchart.

In addition, each step may represent a module, a segment, or a portion of codes which contains one or more executable instructions for executing the specified logical function(s). It should also be noted that in some alternative embodiments, the functions mentioned in the steps may occur out of order. For example, two steps illustrated in succession may in fact be performed substantially simultaneously, or the steps may sometimes be performed in a reverse order depending on the corresponding function.

The above description is merely exemplary description of the technical scope of the present disclosure, and it will be understood by those skilled in the art that various changes and modifications can be made without departing from original characteristics of the present disclosure. Therefore, the embodiments disclosed in the present disclosure are intended to explain, not to limit, the technical scope of the present disclosure, and the technical scope of the present disclosure is not limited by the embodiments. The protection scope of the present disclosure should be interpreted based on the following claims and it should be appreciated that all technical scopes included within a range equivalent thereto are included in the protection scope of the present disclosure.

What is claimed is:

1. A handle grip for a bicycle, comprising:
a first grip portion coupled to a first side of a handlebar for the bicycle;
a first electrode portion disposed outside of the first grip portion so that the first electrode portion comes in contact with a first body surface of a user;
a cable portion having one end connected to the first electrode portion and another end extending outwardly from the first grip portion; and
a module accommodating portion provided in a portion of the first grip portion and having a module space for accommodating a predetermined electronic module;
a second grip portion coupled to a second side of the handlebar for the bicycle; and
a second electrode portion disposed outside the second grip portion so that the second electrode portion comes in contact with a palm of the user when the user grips the second grip portion,
wherein the cable portion connects the first electrode portion to the second electrode portion,
wherein the first electrode portion includes a first input electrode and a first output electrode, and the second electrode portion includes a second input electrode and a second output electrode, and
wherein the cable portion includes:
a first wire configured to connect the first input electrode to the second input electrode;
a second wire configured to connect the first output electrode to the second output electrode; and
an outer insulation configured to electrically insulate the first wire and the second wire from each other.

2. The handle grip of claim 1, further comprising
an electronic module operated to flow a current to the first electrode portion, wherein the electronic module includes:
a power supply unit configured to supply the current to the first electrode portion;
a control unit configured to control the current supplied to the first electrode portion, and measure an electrical characteristic of the first electrode portion when a body of the user comes in contact with the first electrode portion; and
a communications unit configured to transfer information on the electrical characteristic to an external device.

3. The handle grip of claim 2, wherein the control unit performs control so that electricity is supplied to the first electrode portion to measure an electrical characteristic flowing through the first electrode portion when a preset touch pattern is sensed in the first electrode portion.

4. The handle grip of claim 1, wherein the first grip portion includes a cutout portion formed by cutting out a portion of a material coupled to the handlebar in an axial direction of the handlebar so that the first grip portion is attachable to or detachable from the handlebar.

5. The handle grip of claim 1, wherein the module space is formed such that the first grip portion is located at a distal end portion of the handlebar in a state in which the first grip portion is coupled to the handlebar.

6. The handle grip of claim 5, wherein the first grip portion includes an inner grip portion and an outer grip portion configured to be opened and closed with reference to the module space.

7. The handle grip of claim 6, wherein the outer grip portion is made to have a higher strength than that of the inner grip portion.

8. A body composition measurement system, comprising:
a handle grip including a first grip portion coupled to a first side of a handlebar for a bicycle, a first electrode portion disposed outside of the first grip portion so that the first electrode portion comes in contact with a first body surface of a user, a cable portion having one end connected to the first electrode portion and another end extending outwardly from the first grip portion, and an electronic module configured to perform control so that a current flows through the first electrode portion, measure an electrical characteristic of the first electrode portion, and transfer the electrical characteristic to a user terminal; and the user terminal including at least one memory configured to store instructions for performing a predetermined operation, and at least one processor operably connected to the at least one memory and operating to execute instructions for determining a body composition information of the user based on the electrical characteristic, wherein the at least one processor is configured to:
  receive a first electrical characteristic measured with the handle grip at a first point in time before the user rides the bicycle, and determine a first body composition information,
  receive a second electrical characteristic measured with the handle grip at a second point in time after the user rides the bicycle, and determine a second body composition information, and
  provide a newly derived information by utilizing body composition change information generated by comparing the first body composition information with the second body composition information, and by utilizing an information on an event performed by the user between the first point in time and the second point in time.

9. The body composition measurement system of claim 8, wherein the at least one processor is further configured to:
  store a course along which the user moves by a bicycle between the first point in time and the second point in time,
  derive a score by applying a predetermined algorithm to a degree of change in the first body composition information and the second body composition information,
  map the score to the course, and
  provide the score mapped for each course, in order to provide the newly derived information.

10. The body composition measurement system of claim 8, wherein the at least one processor is further configured to:
  receive electrical characteristic measured with the handle grip for each date on which the user rides the bicycle to determine and store the body composition information for each date,
  store a bicycle use time, moving distance, and exercise course based on real-time position information measured for each date on which the user uses the bicycle, and
  provide the bicycle use time, moving distance, exercise course, and body composition information for each date.

11. The body composition measurement system of claim 10, wherein the at least one processor is further configured to:
  receive target body composition information and target date from the user, and
  compare the body composition information measured for each date with the target body composition information to recommend an amount of exercise, an exercise course, an exercise time, and an exercise distance to be performed to achieve the target body composition information by the target date.

12. The body composition measurement system of claim 8, wherein the at least one processor is further configured to:
  receive the electrical characteristic measured with the handle grip by the user to determine the body composition information,
  analyze a muscle mass of a left arm, right arm, left leg, and right leg of the user based on the body composition information, and
  recommend an exercise product for reinforcing a portion whose muscle mass is determined to be smaller than or equal to a preset value among the left arm, right arm, left leg, and right leg of the user.

13. A non-transitory computer-readable recording medium having a computer program stored therein, the computer program comprising instructions for causing a processor to perform a method including:
  receiving an electrical characteristic of a first electrode portion from a handle grip including a first grip portion coupled to a first side of a handlebar for a bicycle, the first electrode portion disposed outside of the first grip portion so that the first electrode portion comes in contact with a first body surface of a user, a cable portion having one end connected to the first electrode portion and another end extending outwardly from the first grip portion, and an electronic module configured to perform control so that a current flows through the first electrode portion, and measure the electrical characteristic of the first electrode portion; and
  determining body composition information of the user based on the electrical characteristic, when the computer program is executed by the processor, wherein the determining of the body composition information of the user includes:
    receiving a first electrical characteristic measured with the handle grip at a first point in time before the user rides the bicycle, and determining first body composition information;
    receiving a second electrical characteristic measured with the handle grip at a second point in time after the user rides the bicycle, and determining second body composition information; and
    providing information derived newly by utilizing body composition change information generated by comparing the first body composition information with the second body composition information, and information on an event performed by the user between the first point in time and the second point in time.

14. The non-transitory computer-readable recording medium of claim 13, wherein the providing of the newly derived information includes:
  storing a course along which the user moves by the bicycle between the first point in time and the second point in time;
  deriving a score by applying a predetermined algorithm to a degree of change in the first body composition information and the second body composition information;
  mapping the score to the course; and
  providing the score mapped for each course.

15. The non-transitory computer-readable recording medium of claim 13, wherein the determining of the body composition information of the user includes:
  receiving electrical characteristic measured with the handle grip for each date on which the user rides the bicycle to determine and store the body composition information for each date;
  receiving target body composition information and target date from the user; and
  comparing the body composition information measured for each date with the target body composition information to recommend an amount of exercise, an exercise course, an exercise time, and an exercise distance to be performed to achieve the target body composition information by the target date.

16. The non-transitory computer-readable recording medium of claim 13, wherein the determining of the body composition information of the user includes:
    receiving the electrical characteristic measured with the handle grip by the user to determine the body composition information,
    analyzing a muscle mass of a left arm, right arm, left leg, and right leg of the user based on the body composition information, and
    recommending an exercise product for reinforcing a portion whose muscle mass is discriminated to be smaller than or equal to a preset value among the left arm, right arm, left leg, and right leg of the user.

\* \* \* \* \*